(12) United States Patent
Seo

(10) Patent No.: US 8,797,236 B2
(45) Date of Patent: Aug. 5, 2014

(54) AUTOMATIC SHADING GOGGLES

(75) Inventor: Woon Su Seo, Gwangmyeong-si (KR)

(73) Assignee: Servore Co., Ltd, Gyeonggi-Do (KR)

( * ) Notice: Subject to any disclaimer, the term of this patent is extended or adjusted under 35 U.S.C. 154(b) by 104 days.

(21) Appl. No.: 13/372,972

(22) Filed: Feb. 14, 2012

(65) Prior Publication Data

US 2012/0204303 A1    Aug. 16, 2012

(30) Foreign Application Priority Data

Feb. 15, 2011    (KR) .................. 10-2011-0013104

(51) Int. Cl.
*G09G 5/00*    (2006.01)

(52) U.S. Cl.
USPC ............. 345/8; 345/87; 345/158; 2/15; 2/6.3; 2/8.2; 2/426; 359/600; 359/643

(58) Field of Classification Search
CPC .................... G06F 17/30115; G06F 17/30129; G06F 17/5004
USPC .......... 345/8, 633, 87–89, 156–158; 2/12, 15, 2/426, 431, 441–444, 6.7, 6.3, 8.2; 359/600, 643, 634, 722, 738; 349/14, 349/117, 121, 161, 171, 87, 95
See application file for complete search history.

(56) References Cited

U.S. PATENT DOCUMENTS

| 5,463,428 | A | * | 10/1995 | Lipton et al. | .................. 351/158 |
| 5,802,622 | A | * | 9/1998 | Baharad et al. | .................. 2/434 |
| 6,015,177 | A | * | 1/2000 | Tijerina | ....................... 296/37.6 |
| 8,081,262 | B1 | * | 12/2011 | Perez | .............................. 349/14 |
| 2007/0013863 | A1 | * | 1/2007 | Zelazowski | ..................... 351/47 |

* cited by examiner

*Primary Examiner* — Lun-Yi Lao
*Assistant Examiner* — Md Saiful A Siddiqui
(74) *Attorney, Agent, or Firm* — IPLA P.A.; James E. Bame

(57) ABSTRACT

Provided is automatic shading goggles in that a welding helmet is manufactured in a goggle shape, so that the size thereof is compact and the weight thereof is light and a shading degree of a LCD lens can be selectively adjusted in any one mode of a welding mode for shielding a harmful light generated during welding operation and a security mode for shielding a visible ray, so that it can reduce a burden of the weight applied to a worker, block a strong light during welding operation, and easily distinguish the surrounding objects, when the welding operation is not performed.

8 Claims, 3 Drawing Sheets

AUTOMATIC SHADING GOGGLES

CROSS REFERENCES

Applicant claims foreign priority under Paris Convention to Korean Patent Application No. 10-2011-0013104 filed 13 Feb. 2011, with the Korean Intellectual Property Office, where the entire contents are incorporated herein by reference.

BACKGROUND OF THE INVENTION

1. Field of the Invention

The present invention relates to an automatic shading goggles, and more particularly to automatic shading goggles in that a welding helmet is manufactured in a goggle shape, so that it can reduce a burden of the weight applied to the worker, block a strong light during welding operation, and easily distinguish the surrounding objects, when the welding operation is not performed.

2. Description of the Prior Art

Generally, the welding is a technique of jointing same or different kinds of metal materials by partially applying a heat and a pressure to them at the same time. During the welding, since a strong light (arc) is emitted and broken pieces are generated, where the worker's eye is exposed to the strong light, it can cause loss of vision of the worker and inflict an injury on his eyeball etc. owing to the broken pieces.

Accordingly, in industrial settings, the work wears a welding helmet for protecting the eyeball and faces thereof from the strong light or broken pieces generated during the welding operation or cutting operation etc.

FIG. 1 is a schematic perspective view illustrating a conventional welding helmet.

As shown in FIG. 1, the conventional welding helmet includes a welding mask 110 for covering the entire face of the wearer, a wearing band 120 for wearing the welding mask 110 on a head of the wearer and rotating the welding mask 110 at a predetermined angle upward and downward and coupled to the welding mask 110 through a rotating axis 121, a light detecting sensor (not shown) for detecting the strong light and generating a driving signal during the generation of the strong light formed at one side of the welding mask 110, a LCD cartridge 130 for protecting the eye of the wearer from the strong light generated during the operation thereof by varying the shading degree of shading the light according the driving signal and formed at a location corresponding to the eye of the wearer, and a front cover 140 for protecting the LCD cartridge 130 and formed at the front side of the LCD cartridge 130.

According to the conventional welding helmet, where the strong light (arc) is generated during the welding operation, the light detecting sensor detects the strong light and generates the driving signal and the light transmission of the LCD cartridge 130 becomes lower according to the generated driving signal to block the strong light.

By the way, since the conventional welding helmet is manufactured to a comparatively large size for covering the face of the worker, it lays heavy strain on the neck of the worker owing to the weight thereof and the storage is not easy owing to the big size thereof.

Also, as described above, in the conventional welding helmet, in order to block the strong light generated during the welding operation, since the light transmission of the LCD cartridge 130 is remarkably lowered, there is a problem in that it is difficult to distinguish the surrounding objects.

Accordingly, where the worker intends to combine the welding operation with another operation, since the attaching and deattaching operations of the welding helmet are repeatedly performed, it is quite cumbersome to do. Also, in case of a manager in a work zone of managing various operations at the same time, in a state that the worker grasps the eye shield for protecting his eye from the broken pieces of the metalwork and the strong visible rays and the welding helmet for protecting his eye from the strong light generated during the welding operation, since he selectively uses the eye shield and the welding helmet, it is quite cumbersome to do. Moreover, because he purchases the eye shield and the welding helmet separately, the financial burden is increased owing to the purchase thereof. Furthermore, since the eye shield and the welding helmet are stored separately, there is a problem in that is very cumbersome to maintain them.

SUMMARY OF THE INVENTION

Accordingly, the present invention has been made to solve the above-mentioned problems occurring in the prior art, and an object of the present invention is to provide automatic shading goggles in that a welding helmet is manufactured in a goggle shape, so that the size thereof is compact and the weight thereof is light and a shading degree of a LCD lens can be selectively adjusted in any one mode of a welding mode for shielding a harmful light generated during welding operation and a security mode for shielding a visible ray, so that it can reduce a burden of the weight applied to a worker, block a strong light during welding operation, and easily distinguish the surrounding objects, when the welding operation is not performed.

Another object of the present invention is to provide automatic shading goggles in that a skirt part of a soft silicon is coupled to a rear surface of an inside body and a front part of the skirt is corresponded to the shape of the inner surface of the inside body, so that it can remarkably improve a bonding force between the skirt part and the inside body and the wearing sensation thereof.

Another object of the present invention is to provide automatic shading goggles in that air vents are formed at one side of the front body, so that the air is circulated to the inside and outside of the skirt part, thereby it can previously prevent the condensation from being occurred on the LCD lens owing to the heat generated from an eyeball of the worker.

To accomplish the object, the present invention provides automatic shading goggles comprising: an inside body having a rear surface formed in a shape corresponding to a curvature of a worker's face and a pair of first openings in front; a front body formed at a front surface of the inside body and having a pair of second openings formed at one surface thereof corresponding to the first openings; a skirt part of a soft material coupled to a rear surface of the inside body and adhered to the worker's face; a fixing member coupled to both side ends of the inside body and fixed to a head part of the worker so as to allow the skirt part to be adhered to the worker's face; a LCD lens for covering the pair of first openings interposed between the inside body and the front body; a light detecting sensor formed at one side of the inside body, detecting a light over a pre-set value and generating a driving signal when the light over the pre-set value is generated from an outside; a control panel formed at one side of the inside body, electrically connected to the LCD lens and the light detecting sensor, supplying a voltage to the LCD lens, and varying a light transmission of the LCD lens during receiving of the driving signal of the light detecting sensor; and a power supply formed at one side of the inside body and supplying a power to the control panel.

Preferably, the automatic shading goggles further comprises a protective lens for covering the pair of the second openings formed at the front surface of the front body.

Preferably, the inside body comprises a pair of first extending parts extended from both sides thereof to the rear thereof, the front body comprise a pair of second extending parts extended from both sides thereof to the rear thereof and corresponded to the pair of the first extending parts respectively, and the control panel and the power supply are formed at both end portions of the inside body so as to be interposed between the first extending parts and the second extending parts.

Preferably, a pair of the LCD lens is formed at the front surface of the inside body and each outside end portion of the LCD lens is slanted at an angle of 3-7 degrees toward the rear thereof.

Preferably, at least one air vent is formed at one side of the front body.

Preferably, a screw hole is formed on one side of the inside body and the skirt part comprises a tightly contacting part corresponding to an outer circumference shape of the rear surface of the inside body and a coupling part corresponded to the inner surface of the inside body, extended from the tightly contacting part toward the front part thereof, and having a screw hole formed on one side thereof corresponding to the screw hole, the coupling part being screw-coupled to the inside body.

Preferably, the inside body comprises a fixing piece corresponded to an outer circumference of the LCD lens formed on the front thereof and protruded from one side to the front portion thereof so as to support the LED lens on the fixing piece, and the front body having a fixing protrusion protruded from one side of the inner surface thereof to the rear thereof and pressing and fixing one side of the LED lens supported by the fixing piece thereto when the front body is coupled to the front surface of the inside body.

Preferably, the control panel allows the voltage to be selectively applied to the LCD lens so as to be driven in any one mode of a welding mode for shielding a harmful light generated during welding operation and a security mode for shielding a visible ray.

Preferably, an attaching and deattaching recess, which is corresponding to a shape of a separate powerful spectacles frame, is formed at the inside of the rear surface of the skirt part.

BRIEF DESCRIPTION OF THE DRAWINGS

The above as well as the other objects, features and advantages of the present invention will be more apparent from the following detailed description taken in conjunction with the accompanying drawings, in which.

DETAILED DESCRIPTION OF THE EXEMPLARY EMBODIMENTS

Hereinafter, preferred embodiments of the present invention will be described with reference to the accompanying drawings.

Figure 1:
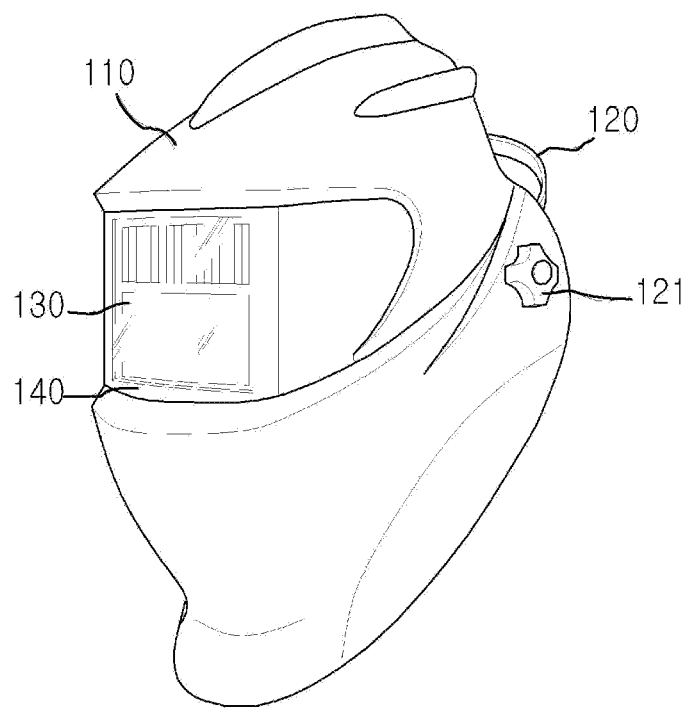
FIG. 1 is a schematic perspective view illustrating a conventional welding helmet.
Figure 2:
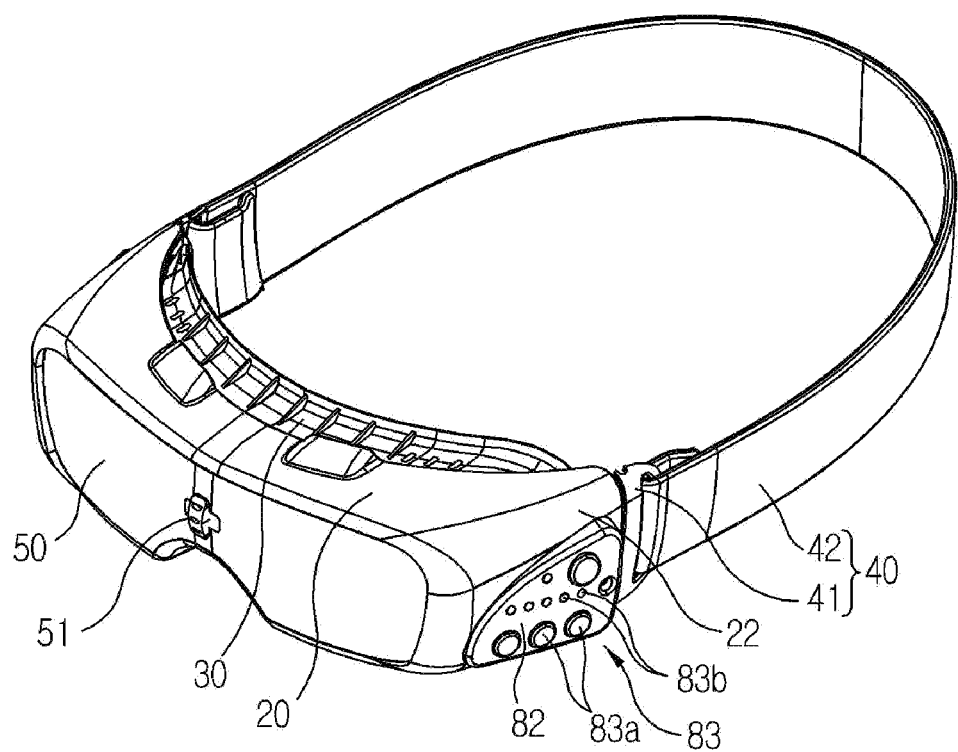
FIG. 2 is a perspective view illustrating automatic shading goggles according to the present invention.
Figure 3:
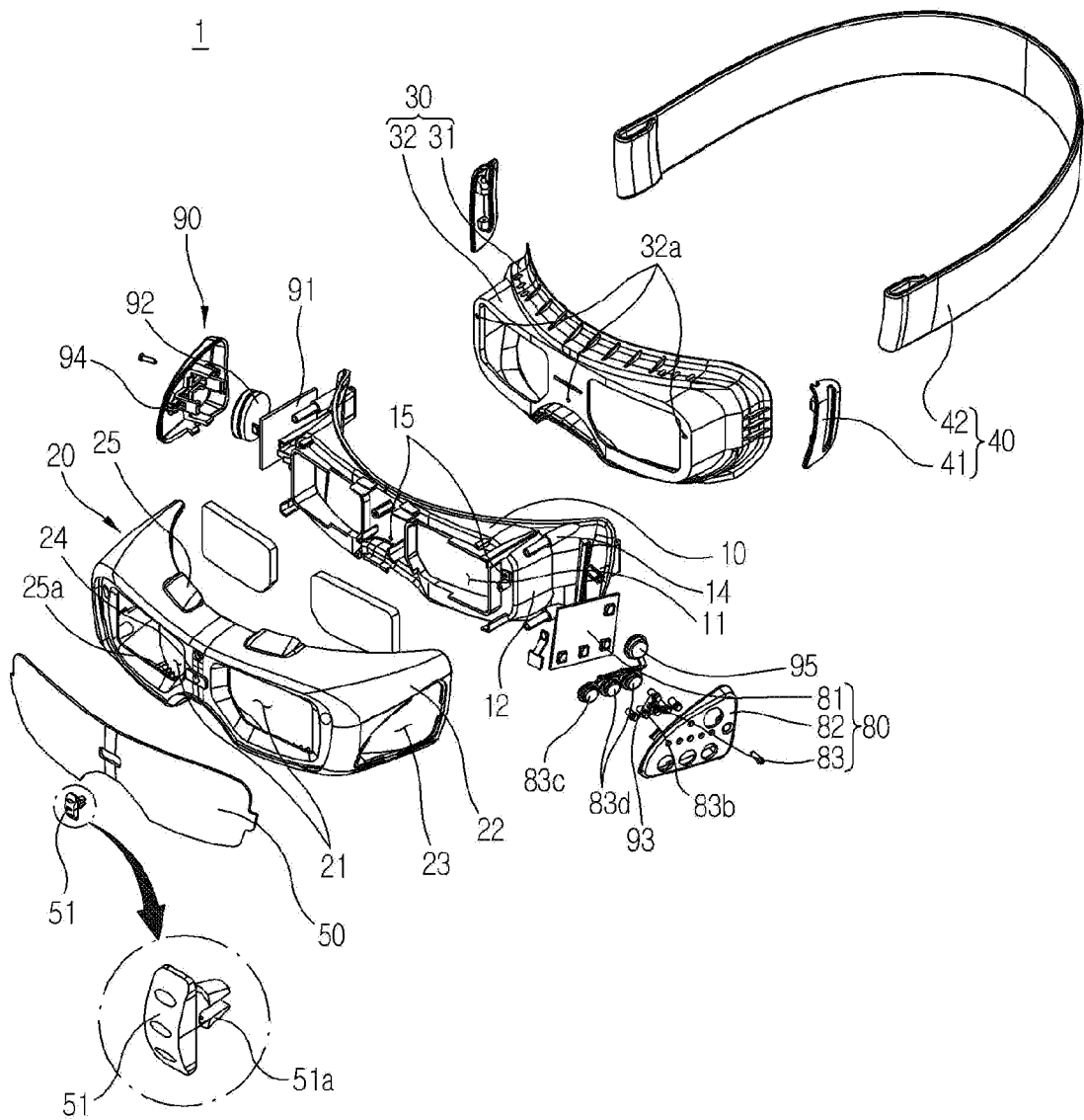
FIG. 3 is an exploded perspective view illustrating automatic shading goggles according to the present invention.

FIG. 2 is a perspective view illustrating automatic shading goggles according to the present invention and FIG. 3 is an exploded perspective view illustrating automatic shading goggles according to the present invention.

As shown in FIG. 2 and FIG. 3, the automatic shading goggles 1 according to the present invention includes an inside body 10, a front body 20, a skirt part 30, a fixing member 40, a protective lens 50, LCD lens 60, a light detecting sensor 70, a control panel 80, and a power supply 90.

The inside body 10 includes a pair of first openings 11 in front and a pair of first extending parts 12 extended from both sides thereof to the rear thereof. The inside body 10 serves to provide an installation space of the LCD lens 60, the control panel 80, and the power supply 90.

Also, the inside body 10 includes a plurality of fixing pieces 13 corresponded to an outer circumference of the LCD lens 60 for covering the pair of first openings 11 formed on the front thereof and protruded from one side to the front portion thereof.

The fixing piece 13 is formed at one side of the front surface of the inside body 10. The fixing piece 13 serves to support one side of the outer circumference of the LED lens 60 and allow the LED lens 60 to be arranged on the front portion of the inside body 10.

Moreover, the inside body 10 further includes a plurality of coupling pillars 14 coupled to the front body 20 and extended from one side of an outside surface of the first extending part 12 to the front thereof and a plurality of coupling holes 15 formed on one side of the front portion thereof and coupled to the following skirt part 30 by means of a screw.

The front body 20 includes a pair of second openings 21 corresponding to the first openings 11 in front and a pair of second extending parts 22 extended from both sides thereof to the rear thereof and corresponded to the pair of the first extending parts 12 respectively and exposure holes 23 formed on one side of the pair of the second extending parts 22 so as to expose a cover of the control panel 80 and a cover of the power supply 90 to outside.

The front body 20 includes a coupling recess 24 formed between the pair of the second openings 21 and coupled to a coupling protrusion 51a of the following protective lens fastener 51.

The above front body 20 serves to form an external shape in general and provide an installation space of the protective lens 50 so as to install the protective lens 50 therein.

Also, the front body 20 further includes ventilation parts 25 protruded toward an upper part and a lower part thereof on the upper and lower surfaces thereof respectively and a plurality of air vents 25a formed on one side of the ventilation parts 25 so as to allow the air to be circulated to the inside and outside of the skirt part 30 through the air vents 25a during wearing of the automatic shading goggles 1, thereby it can previously prevent the condensation from being occurred on the following LCD lens 60 owing to the heat generated from an eyeball of the worker.

Also, it is preferred that the front body 20 includes a fixing protrusion (not shown) protruded from one side of the inner surface thereof to the rear thereof and pressing and fixing one side of the LED lens supported by the fixing piece 13 thereon, when the front body 20 is coupled to the front surface of the inside body.

The skirt part 30 includes a tightly contacting part 31 corresponding to an outer circumference shape of the rear surface of the inside body 10 and a coupling part 32 corresponded to the inner surface of the inside body 10 and protruded from the front surface of the tightly contacting part 31 toward the front part thereof.

Here, the coupling part 32 includes a plurality of screw holes 32a formed on one side thereof corresponding to the coupling holes 15 of the inside body 10. Accordingly, the screws are inserted to the screw holes 32a, so that the skirt part can be strongly coupled to the inside body 10.

At this time, where the skirt part 30 is screw-coupled to the inside body 10, a support plate (not shown) having holes is arranged on one side of the skirt part, on which the screw holes 32a are formed, and the screws are inserted into the screw holes 32a and the coupling holes 15 through the holes of the support plate, so that the head parts of the screws are supported by the support plate, thereby it can prevent the skirt part 30 made of a soft silicon from being damaged owing to the screws and can be more strongly screw-coupled.

The above skirt part 30 made of the soft silicon can be strongly coupled to the inside body 10. Also, the skirt part is adhered to the face of the worker, thereby improving the wearing sensation.

Also, an attaching and deattaching recess (not shown), which is corresponding to a shape of a separate powerful spectacles frame, is formed at the inside of the rear surface of the skirt part 30, the worker of wearing glasses can wear the powerful spectacles frame, to which a lens having a lens prescription corresponding to the worker's glasses is coupled, so that the powerful spectacles frame can be inserted into the attaching and deattaching recess during wearing of the automatic shading goggles 1 according to the present invention, thereby the worker of wearing glasses can easily perform the operation thereof.

The fixing member 40 includes a pair of hooks 41 coupled to both side surface of the inside body 10 respectively and a band part 42 of an elastic material having both end parts coupled to the pair of hooks 41 respectively. The band part 42 is fixed to the head of the worker, so that the rear surface of the skirt part 30 can be adhered to the face of the worker.

As described above, the fixing member 40 of the automatic shading goggles 1 according to the present invention includes the hooks 41 and the band part 42. However, if the skirt part 30 is adhered to the face of the worker, it is not limited to the construction of the fixing member.

The protective lens 50 is made of a transparent material and formed at one side of the front surface of the front body 20, so that it can previously prevent the following LCD lens 60 from being damaged owing to the broken pieces generated during welding.

The above protective lens 50 includes the protective lens fastener 51 having the coupling protrusion 51a formed on one side thereof. One side of the protective lens fastener 51 is penetrated therethrough. The coupling protrusion 51a of the following protective lens fastener 51 is coupled to the coupling recess 24 of the front body 20, so that it can be strongly fixed to the front body 20.

The pair of the LCD lens 60 having a plate shape is arranged on the front surface of the inside body 10 and the outer circumference of the LCD lens 60 is supported by the plurality of the fixing pieces 13. Here, where the front body 20 is coupled to the inside body 10, the outer circumference area of the front surface of the LCD lens 60 is supported by and fixed to one side of the inner surface of the front body 20.

The LCD lens 60 is driven in a welding mode for shielding a harmful light generated during welding operation or a security mode for shielding the strong visible ray according to the voltage values supplied from the following control panel 80.

Accordingly, the LCD lens 60 according to the present invention is driven in the welding mode for shielding the harmful light during welding operation, so that it can protect the worker's eye from the harmful light. Also, where the welding operation is not conducted, the LCD lens 60 is driven in the security mode for shielding only the strong visible, so that it can easily distinguish the surrounding objects. Therefore, it is characterized in that the welding operation, in that the harmful light is generated, and the general operation, in that the harmful light is not generated, can be easily combined.

Also, each outside end portion of the protective lens 50 and the LCD lens 60 is slanted at an angle of 3-7 degrees toward the rear thereof so as to extend the viewing angle of the worker.

The light detecting sensor 70 is formed at the control panel 80 and the power supply 90 one by one. The light detecting sensor 70 serves to detect a light generated from outside and generate a driving signal.

The above light detecting sensor 70 may be a common photodiode. Since the photodiode is well-known in the art, a concrete description on this is omitted here.

The control panel 80 includes a control printed circuit board 81 electrically connected to the LCD lens 60 and the light detecting sensor 70, a first cover 82 for covering the control printed circuit board 81 coupled to one side of the inside body 10 corresponding to the control printed circuit board 81, a shading degree adjusting part 83 having one end portion exposed to outside and another end portion electrically contacted to one side of the control printed circuit board 81, so that the shading degree of the LCD lens 60 can be controlled.

Here, the control printed circuit board 81 receives the driving signal from the light detecting sensor 70 and supplies the voltage to the LCD lens 60, so that the LCD lens 60 can be driven in the security mode or the welding mode.

The shading degree adjusting part 83 includes a mode selection button 83a for sending the driving signal to the control printed circuit board 81 so as to drive the LDC lens 60 in the security mode or the welding mode according to a selection of a step of the shading degree, a shading degree display LED 83b for distinguishing a change of the step of the shading degree by the worker when the step of the shading degree is changed by means of the mode selection button 83a, a hold button 83c for maintaining the present shading degree according to the selection of the worker in the security mode, and a sensor sensitivity button 83d for adjusting a sensor sensitivity of the light detecting sensor 70. Accordingly, where the mode selection button 83a selected by the worker is electrically contacted to the control printed circuit board 81, the shading degree adjusting part 83 serves to send the variable signal of the shading degree to the control printed circuit board 81 so as to vary the shading degree of the LCD lens 60.

The power supply 90 includes a power printed circuit board 91 electrically connected to the LCD lens 60 and the control printed circuit board 81 to supply the power thereto, a battery 92 contacted to the power printed circuit board 91, a light emitting diode 93 formed on one side of the inside body 10, a second cover 94 for covering the power printed circuit board 91 coupled to one side of the inside body 10 corresponding to the power printed circuit board 91. The power supply 90 serves to supply the power to the LCD lens 60 and the control printed circuit board 81 and detect the voltage of the battery below the pre-set voltage value to display a low voltage through the light emitting diode 93.

Also, the power supply 90 includes a power button 95 for turning on or turning off the power.

Also, the control panel 80 and the power supply 90 are exposed to outside through the exposure holes 23, the cover of the control panel 80 and the cover of the power supply 90, so that the component parts of the control panel 80 and the power supply 90 can be easily changed or repaired.

Hereinafter, the operation of the automatic shading goggles 1 according to the present invention will be described with reference to FIG. 3.

Firstly, where the worker wears the automatic shading goggles 1 according to the present invention and performs the welding operation, if the harmful light (arc) is generated, the light detecting sensor 70 detects the generated harmful light.

Then, the driving signal is generated from the light detecting sensor 70 and then, the control printed circuit board 81 receives the driving signal. Thereafter, the voltage is supplied to the LCD lens 60 to be driven in a pre-set shading degree grade.

Continuously, the worker adjusts the shading degree adjusting part 83 according to the intensity of the harmful light of the welding operation, so that the shading degree of the LCD lens 60 is adjusted in the welding mode to perform the welding operation.

Here, where the welding operation is completed or the worker intends to perform another operation, the worker adjusts the shading degree adjusting part 83, so that the shading degree of the LCD lens 60 is changed from the welding mode to the security mode. Thereafter, when the worker distinguishes the surrounding objects, he performs the desired operation.

While this invention has been described in connection with what are presently considered to be the most practical and preferred embodiments, it is to be understood that the invention is not limited to the disclosed embodiments and the drawings, but, on the contrary, it is intended to cover various modifications and variations within the spirit and scope of the appended claims.

What is claimed is:

1. Automatic shading goggles comprising:
    an inside body having a rear surface formed in a shape corresponding to a curvature of a worker's face and a pair of first openings in front;
    a front body formed at a front surface of the inside body and having a pair of second openings formed at one surface thereof corresponding to the first openings;
    a skirt part of a soft material coupled to a rear surface of the inside body and adhered to the worker's face;
    a fixing member coupled to both side ends of the inside body and fixed to a head part of the worker so as to allow the skirt part to be adhered to the worker's face;
    a LCD lens for covering the pair of first openings interposed between the inside body and the front body;
    a light detecting sensor formed at one side of the inside body, detecting a light over a pre-set value and generating a driving signal when the light over the pre-set value is generated from an outside;
    a control panel formed at one side of the inside body, electrically connected to the LCD lens and the light detecting sensor, supplying a voltage to the LCD lens, and varying a light transmission of the LCD lens during receiving of the driving signal of the light detecting sensor; and
    a power supply formed at one side of the inside body and supplying a power to the control panel,
    wherein a coupling hole is formed on one side of the inside body,
    wherein the skirt part comprises a tightly contacting part corresponding to an outer circumference shape of the rear surface of the inside body and a coupling part corresponding to the inner surface of the inside body, extended from the tightly contacting part toward the front part thereof, and having a screw hole formed on one side thereof corresponding to the coupling hole, the coupling part of the skirt part being screw-coupled to the inside body.

2. Automatic shading goggles as claimed in claim 1, further comprising a protective lens for covering the pair of the second openings formed at the front surface of the front body.

3. Automatic shading goggles as claimed in claim 1, wherein the inside body comprises a pair of first extending parts extended from both sides thereof to the rear thereof, the front body comprise a pair of second extending parts extended from both sides thereof to the rear thereof and corresponded to the pair of the first extending parts respectively, and the control panel and the power supply are formed at both end portions of the inside body so as to be interposed between the first extending parts and the second extending parts.

4. Automatic shading goggles as claimed in claim 1, wherein a pair of the LCD lens is formed at the front surface of the inside body and each outside end portion of the LCD lens is slanted at an angle of 3-7 degrees toward the rear thereof.

5. Automatic shading goggles as claimed in claim 1, wherein at least one air vent is formed at one side of the front body.

6. Automatic shading goggles as claimed in claim 1, wherein the inside body comprises a fixing piece corresponded to an outer circumference of the LCD lens formed on the front thereof and protruded from one side to the front portion thereof so as to support the LED lens on the fixing piece, and the front body having a fixing protrusion protruded from one side of the inner surface thereof to the rear thereof and pressing and fixing one side of the LED lens supported by the fixing piece thereon when the front body is coupled to the front surface of the inside body.

7. Automatic shading goggles as claimed in claim 1, wherein the control panel allows the voltage to be selectively applied to the LCD lens so as to be driven in any one mode of a welding mode for shielding a harmful light generated during welding operation and a security mode for shielding a visible ray.

8. Automatic shading goggles as claimed in claim 1, wherein an attaching and detaching recess, which is corresponding to a shape of a separate powerful spectacles frame, is formed at the inside of the rear surface of the skirt part.

\* \* \* \* \*